US009205934B2

(12) United States Patent
Rashkov et al.

(10) Patent No.: US 9,205,934 B2
(45) Date of Patent: Dec. 8, 2015

(54) ADAPTIVE OSCILLATORY FAULT MONITORING

(71) Applicant: Gulfstream Aerospace Corporation, Savannah, GA (US)

(72) Inventors: Ventseslav Rashkov, Pooler, GA (US); Michael Curtis, Guyton, GA (US)

(73) Assignee: Gulfstream Aerospace Corporation, Savannah, GA (US)

( * ) Notice: Subject to any disclaimer, the term of this patent is extended or adjusted under 35 U.S.C. 154(b) by 0 days.

(21) Appl. No.: 14/166,518

(22) Filed: Jan. 28, 2014

(65) Prior Publication Data
US 2014/0214266 A1 Jul. 31, 2014

Related U.S. Application Data

(60) Provisional application No. 61/757,557, filed on Jan. 28, 2013.

(51) Int. Cl.
*B64F 5/00* (2006.01)
*G01R 23/15* (2006.01)
*G01R 31/00* (2006.01)
*G01N 29/12* (2006.01)

(52) U.S. Cl.
CPC .............. *B64F 5/0045* (2013.01); *G01N 29/12* (2013.01); *G01R 23/15* (2013.01); *G01N 2291/2694* (2013.01); *G01R 31/008* (2013.01)

(58) Field of Classification Search
CPC ...... B64F 5/0045; G01R 23/15; G01R 31/008
See application file for complete search history.

(56) References Cited

U.S. PATENT DOCUMENTS

| 4,826,110 | A |   | 5/1989 | Le |
| 5,319,296 | A |   | 6/1994 | Patel |
| 5,598,991 | A |   | 2/1997 | Nadkarni et al. |
| 5,710,776 | A | * | 1/1998 | Tomlinson et al. ........... 714/704 |
| 5,881,971 | A |   | 3/1999 | Hickman |
| 6,121,778 | A | * | 9/2000 | Moore .......................... 324/619 |
| 6,252,411 | B1 | * | 6/2001 | Moore .......................... 324/619 |

(Continued)

OTHER PUBLICATIONS

United States International Searching Authority, International Search Report and Written Opinion for International Application No. PCT/US14/13413, mailed Oct. 1, 2014.

(Continued)

*Primary Examiner* — Yonel Beaulieu
*Assistant Examiner* — Dale W Hilgendorf
(74) *Attorney, Agent, or Firm* — Ingrassia, Fisher & Lorenz, PC (57) ABSTRACT

Systems, media, and methods are provided for oscillation monitoring. An aircraft system includes a first oscillation monitoring module and a second oscillation monitoring module. The first oscillation monitoring module is configured to select first oscillating portions of an input signal, generate a frequency signal that indicates a frequency of the first oscillating portions, and generate a first failure signal in response to the frequency of the first oscillating portions exceeding first oscillatory fault detection requirements for the input signal. The second oscillation monitoring module is configured to select second oscillating portions of the input signal based on the frequency signal generated by the first oscillation monitoring module and to generate a second failure signal in response to a frequency of the second oscillating portions exceeding second oscillatory fault detection requirements for the input signal.

20 Claims, 11 Drawing Sheets

(56) References Cited

U.S. PATENT DOCUMENTS

| | | | |
|---|---|---|---|
| 7,567,862 B2 * | 7/2009 | Pelton et al. | 701/33.8 |
| 7,640,139 B2 * | 12/2009 | Sahara et al. | 702/183 |
| 7,725,224 B2 | 5/2010 | Goupil | |
| 7,933,725 B2 | 4/2011 | Krone | |
| 7,965,805 B2 * | 6/2011 | Lee et al. | 375/371 |
| 8,090,485 B2 | 1/2012 | Grinits et al. | |
| 8,160,770 B2 | 4/2012 | Goupil et al. | |
| 8,234,037 B2 | 7/2012 | Goupil et al. | |
| 2003/0014199 A1 * | 1/2003 | Toomey | 702/56 |
| 2007/0124038 A1 * | 5/2007 | Goupil | 701/3 |
| 2009/0048689 A1 | 2/2009 | Pelton et al. | |
| 2012/0194201 A1 * | 8/2012 | Saloio | 324/537 |
| 2014/0214266 A1 | 7/2014 | Rashkov et al. | |

OTHER PUBLICATIONS

The International Bureau of WIPO, International Preliminary Report on Patentability for International Application No. PCT/US2014/013413 mailed Aug. 6, 2015.

\* cited by examiner

ADAPTIVE OSCILLATORY FAULT MONITORING

CROSS-REFERENCE TO RELATED APPLICATIONS

This application claims the benefit of U.S. Provisional Application No. 61/757,557 filed on Jan. 28, 2013. The disclosure of the above application is incorporated herein by reference.

TECHNICAL FIELD

The technical field relates generally to oscillatory fault detection techniques, and more particularly relates to oscillatory fault detection techniques with adaptive threshold windows.

BACKGROUND

With the rapid developments in aircraft technology, ever-increasing flight envelopes, and overall performance, the flight control systems implemented in modern aircraft have become extremely complex. Advanced flight control systems have therefore been developed to address various aircraft characteristics such as flight performance, fuel efficiency, safety, etc. A primary flight control system on a modern aircraft typically includes a complex set of components including pilot controls, aircraft sensors, electronic processors, electronic wiring or data buses, actuators, and control surfaces. Unfortunately, as the primary flight control system increases in complexity, the aircraft may be increasingly vulnerable to a system fault or processor failure.

One type of failure monitored in aircraft is fatigue failure due to oscillations on the surfaces of the aircraft. The requirements for oscillation monitoring may be very complex, with varying threshold amplitude at different frequencies. A typical oscillation monitor employs digital filters and must be heavily tuned to the specific requirements of the design.

These typical oscillatory monitors are often very complex and may require a mathematical model of the monitored system to generate a fault-indicating signal. Multiple monitoring structures & filters are typically required to cover the entire frequency range of interest. The digital filters often create additional difficulties as the digital filters may cause linear distortions and attenuation of the monitored signal. Furthermore, existing oscillation monitors are typically heavily tuned to a specific requirements curve and failure mode, and therefore may not be easily adapted to a different environment or application.

Accordingly, it is desirable to provide an oscillation monitoring solution that does not rely on digital filters. In addition, it is desirable to provide an oscillation monitoring solution that is robust and readily adaptable to various requirement curves and failure modes. Furthermore, other desirable features and characteristics of the present invention will become apparent from the subsequent detailed description of the invention and the appended claims, taken in conjunction with the accompanying drawings and this background of the invention.

SUMMARY OF EMBODIMENTS

Various non-limiting embodiments of systems, media, and methods are disclosed herein.

In a first non-limiting embodiment, an aircraft system includes a first oscillation monitoring module and a second oscillation monitoring module. The first oscillation monitoring module is configured to select first oscillating portions of an input signal, generate a frequency signal that indicates a frequency of the first oscillating portions, and generate a first failure signal in response to the frequency of the first oscillating portions exceeding first oscillatory fault detection requirements for the input signal. The second oscillation monitoring module is configured to select second oscillating portions of the input signal based on the frequency signal generated by the first oscillation monitoring module and to generate a second failure signal in response to a frequency of the second oscillating portions exceeding second oscillatory fault detection requirements for the input signal.

In a second non-limiting embodiment, a non-transitory computer readable medium stores instructions for execution by a processor. The instructions are configured to cause a processor to select first oscillating portions of an input signal with a first oscillation monitoring module, generate a frequency signal that indicates a frequency of the first oscillating portions, generate a first failure signal in response to the frequency of the first oscillating portions exceeding first oscillatory fault detection requirements for the input signal, select second oscillating portions of the input signal based on the frequency signal generated by the first oscillation monitoring module, and generate a second failure signal at a second oscillation monitoring module in response to a frequency of the second oscillating portions exceeding second oscillatory fault detection requirements for the input signal.

In a third non-limiting embodiment, a method of monitoring oscillations of an input signal includes, but is not limited to, selecting first oscillating portions of the input signal with a first oscillation monitoring module, generating a frequency signal that indicates a frequency of the first oscillating portions, generating a first failure signal in response to the frequency of the first oscillating portions exceeding first oscillatory fault detection requirements for the input signal, selecting second oscillating portions of the input signal based on the frequency signal generated by the first oscillation monitoring module, and generating a second failure signal at a second oscillation monitoring module in response to a frequency of the second oscillating portions exceeding second oscillatory fault detection requirements for the input signal.

BRIEF DESCRIPTION OF THE DRAWINGS

Advantages of the present invention will be readily appreciated, as the same becomes better understood by reference to the following detailed description when considered in connection with the accompanying drawings wherein.

2B is a simplified block diagrams of components of an oscillation monitoring module according to some embodiments.

DETAILED DESCRIPTION

The following detailed description is merely exemplary in nature and is not intended to limit application and uses. As used herein, the word "exemplary" means "serving as an example, instance, or illustration." Thus, any embodiment described herein as "exemplary" is not necessarily to be construed as preferred or advantageous over other embodiments. All of the embodiments described herein are exemplary embodiments provided to enable persons skilled in the art to make or use the disclosed embodiments and not to limit the scope of the disclosure which is defined by the claims. Furthermore, there is no intention to be bound by any expressed or implied theory presented in the preceding technical field, background, brief summary, the following detailed description or for any particular computer system.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. Additionally, the following description refers to elements or features being "connected" or "coupled" together. As used herein, "connected" may refer to one element/feature being directly joined to (or directly communicating with) another element/feature, and not necessarily mechanically. Likewise, "coupled" may refer to one element/feature being directly or indirectly joined to (or directly or indirectly communicating with) another element/feature, and not necessarily mechanically. However, it should be understood that, although two elements may be described below, in one embodiment, as being "connected," in alternative embodiments similar elements may be "coupled," and vice versa. Thus, although the block diagrams shown herein depict example arrangements of elements, additional intervening elements, devices, features, or components may be present in an actual embodiment.

Finally, for the sake of brevity, conventional techniques and components related to computer systems and other functional aspects of a computer system (and the individual operating components of the system) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the disclosure.

Figure 1A:
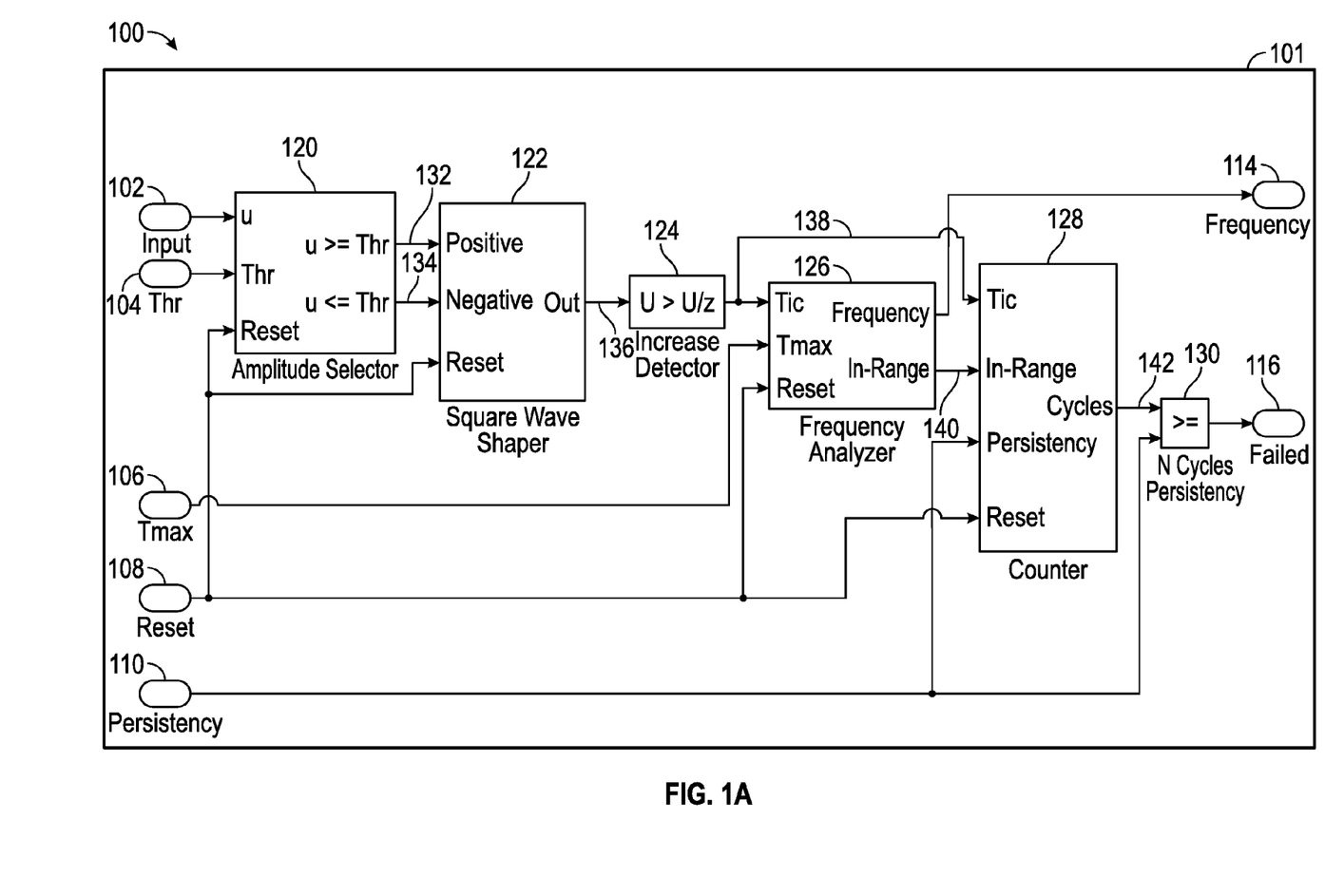
FIG. 1A is a simplified block diagrams of an oscillation monitoring module according to some embodiments.

Referring now to FIG. 1A, an oscillation monitoring module 100 is illustrated in accordance with some embodiments. Although the module 100 is described with respect to flight control system monitoring, it should be appreciated that the module 100 may be utilized to monitor oscillations in other applications and environments. In some embodiments, the module 100 may be implemented as software library blocks in a computer system 101 and may be used as building components of an oscillatory fault monitor, as will be described below. For example, the computer system 101 may be an aircraft system that includes processors, memory, and other components. It should be appreciated that in some embodiments, the module 100 may be implemented in a digital signal processor, an application specific integrated circuit (ASIC), an electronic circuit, a processor (shared, dedicated, or group) and memory that execute one or more software or firmware programs, a combinational logic circuit, and/or other suitable components that provide the described functionality.

The module 100 is configured to receive inputs that include a monitored input signal 102, a magnitude threshold 104, a period threshold 106, a reset input 108, and a persistency threshold 110. For example, the module 100 may include one or more input ports to receive signals associated with the inputs. The monitored input signal 102 may be an output from various types of sensors, output from a controller (such as a flight control computer or a remote electronic unit), or any other signal or command that is to be monitored for oscillations.

The magnitude threshold 104 is based on an oscillatory requirement amplitude that is provided based on the requirements of the system in which the oscillations are monitored. The magnitude threshold indicates an amplitude that is used to calculate an upper threshold and a lower threshold of an adaptive threshold window. For example, the magnitude threshold 104 may indicate the size of the adaptive threshold window or may indicate a fraction (such as one half) of the size of the adaptive threshold window. It should be appreciated that the magnitude threshold 104 input may be received throughout the method described below, and therefore the size of the adaptive threshold window may change over time.

The module 100 is further configured to generate a frequency signal 114 and a failure signal 116 according to the methods described below. For example, the module 100 may include one or two output ports at which signals 114 and 116 are provided.

Figure 1B:
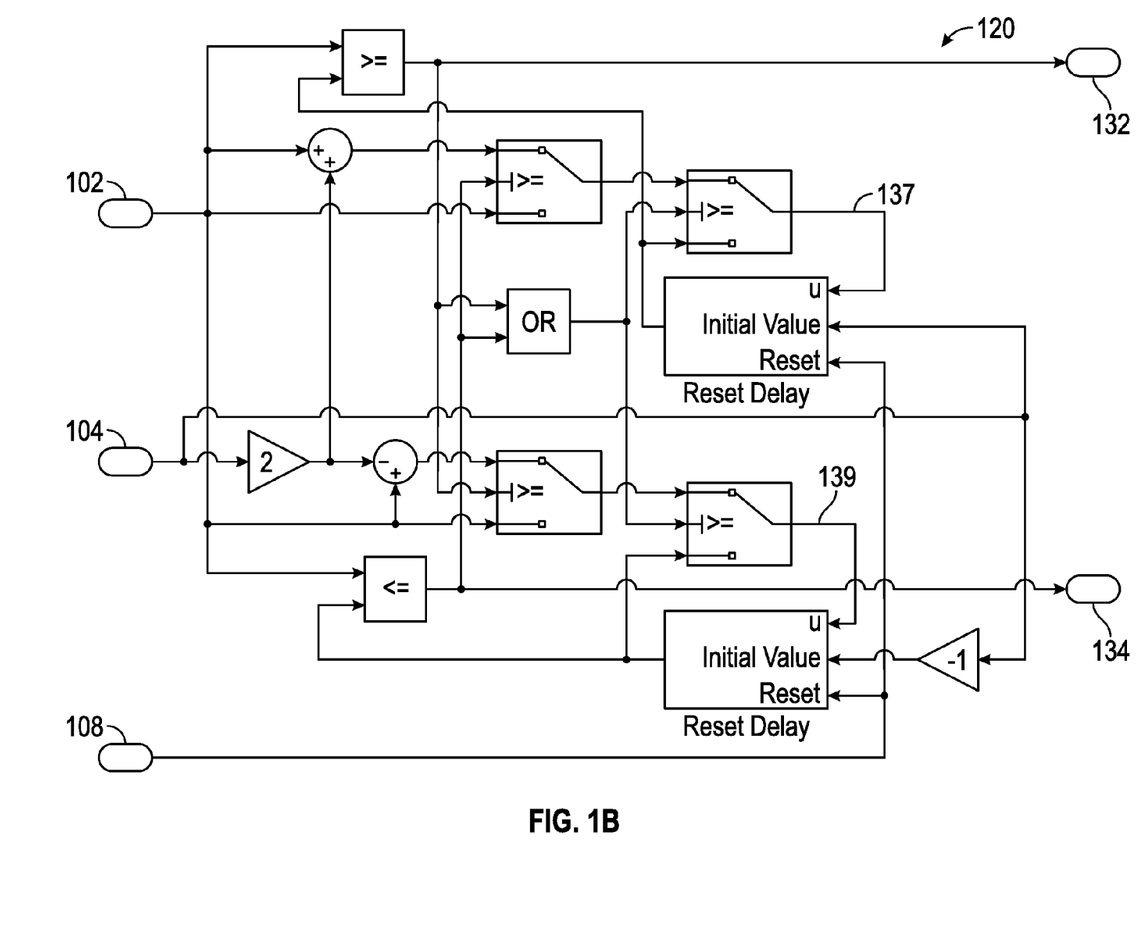
FIGS. 1B, 1D, 1E, and 1F are simplified block diagrams of components of an oscillation monitoring module according to some embodiments.
Figure 1C:
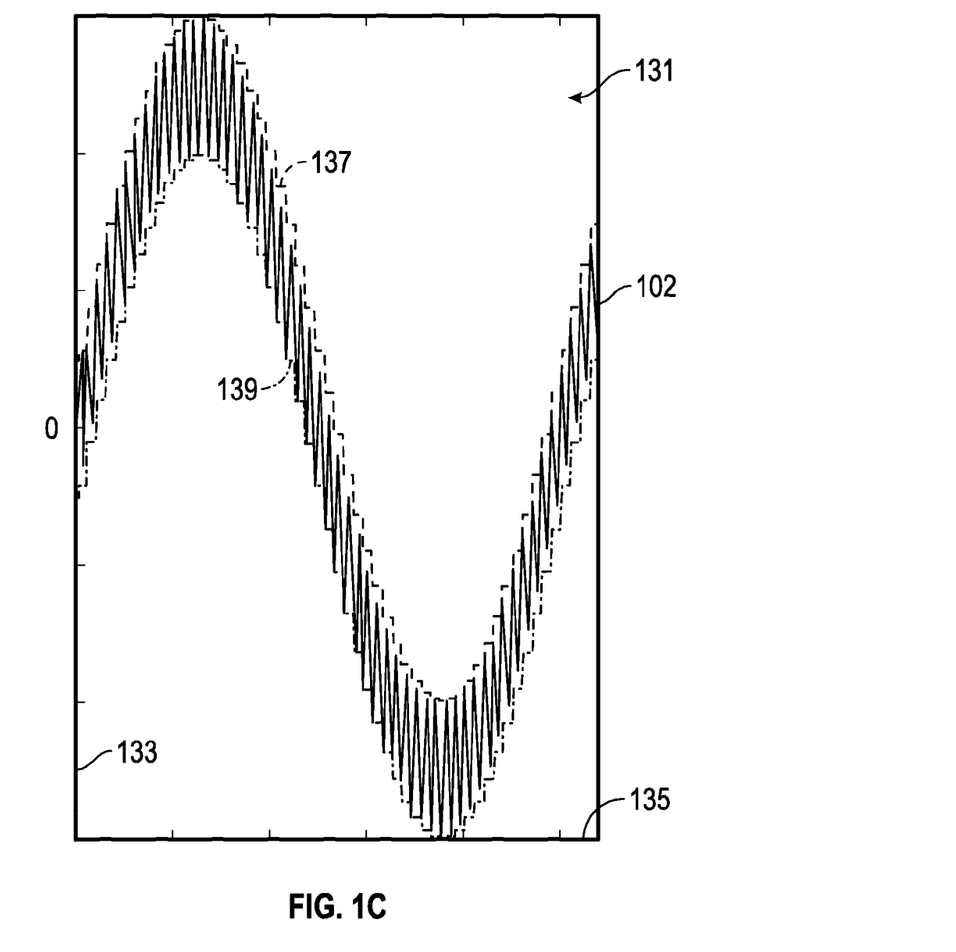
FIG. 1C is a graphical representation of data associated with the oscillation monitoring modules according to some embodiments.

The module 100 includes an amplitude selector 120, a square wave shaper 122, an increase detector 124, a frequency analyzer 126, a counter 128, and a persistency comparison block 130. An example of an amplitude selector 120 is illustrated in FIG. 1B and monitor data 131 is illustrated in FIG. 1C in accordance with some embodiments. It should be appreciated that other implementations may be incorporated to achieve the features of the amplitude selector 120 without departing from the scope of the present disclosure.

The monitored data 131 is graphed with an instant value on a vertical axis 133 and time on a horizontal axis 135. The amplitude selector 120 selects oscillations based on whether the monitored input signal 102 exceeds an upper threshold 137 and a lower threshold 139 that are calculated based on the magnitude threshold 104. The upper and the lower thresholds 137, 139 are self-adaptable to the monitored input signal 102 to create an adaptive threshold window. The adaptive threshold window promotes detection of both "liquid" and "solid" failures and reduces detection sensitivity to input offset, as will be appreciated by those will skill in the art. For example, the adaptive threshold window permits counting the oscillations around zero in the case of a "liquid" failure.

The amplitude selector 120 generates a "positive" discrete signal 132 when the magnitude of the monitored input signal 102 is equal to or greater than the upper threshold 137, such as when the thresholds 137 and 139 are increasing in the monitor data 131 provided. The amplitude selector generates a "negative" discrete signal 134 when the magnitude of the monitored input signal 102 is equal to or less than the lower threshold 139, such as when the thresholds 137 and 139 are decreasing in the monitor data 131 provided. For example, the amplitude selector 120 may set the signals 132 and 134 to "true" when the respective thresholds are exceeded and to "false" when the respective thresholds are not exceeded.

At initialization of the module 100, the upper threshold 137 is determined as the value of the magnitude threshold 104 with positive polarity, and the lower threshold 139 has the same value but with negative polarity. The upper threshold 137 and lower threshold 139 do not change as long as the monitored input signal 102 stays between the upper and lower thresholds 137 and 139. When the magnitude of the monitored input signal 102 exceeds the upper threshold 137, the upper threshold 137 increases to match the monitored input signal 102 as long as the magnitude of the monitored input signal 102 is increasing. The lower threshold 139 increases with the upper threshold 137 to maintain the difference between upper and lower thresholds as indicated by the magnitude threshold 104.

Similarly, when the magnitude of the monitored input signal 102 exceeds the lower threshold 139 (e.g., has a lower value than the lower threshold 139), the lower threshold 139 decreases to match the magnitude of the monitored input signal 102 as long as the magnitude of the monitored input signal 102 is decreasing. The upper threshold 137 decreases with the lower threshold 139 to maintain the difference between upper and lower thresholds as indicated by the magnitude threshold 104. The upper and lower thresholds reset to the initialization values when the amplitude selector 120 receives the reset input 108.

The movement of the thresholds with the magnitude of the input signal 102 permits the threshold window to adapt to various conditions of the input signal 102. For example, the adaptive threshold window promotes robust counting of oscillations with random shape, varying frequency and non-deterministic amplitude, including additive and multiplicative noise. Furthermore, the adaptive threshold window eliminates the need for high-pass filtering to center the monitored input signal on a zero point, which may wash out slowly changing bias.

Figure 1D:
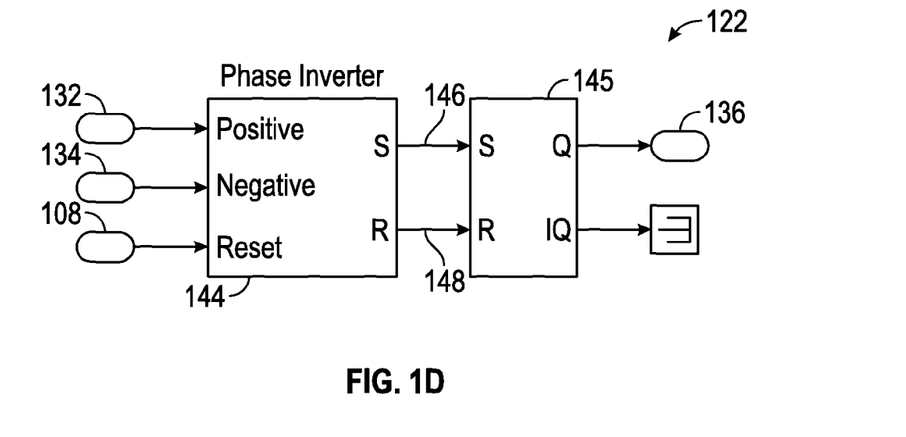

The square wave shaper 122 receives the signals 132, 134, the reset input 108, and generates a square wave signal 136 with normalized amplitude. In the example provided, the square wave shaper 122 includes a phase inverter 144 and a flip-flop latch 145, as illustrated in FIG. 1D. It should be appreciated that other configurations may be utilized to achieve the features of the square wave shaper 122 without departing from the scope of the present disclosure. The phase inverter 144 shifts the phase of the oscillation by 180° when the oscillation starts to the negative direction. The square wave signal 136 therefore starts in the positive direction, regardless of the oscillation phase shift.

The flip-flop latch 145 is used to generate a square wave, based on the set output signal 146 and the reset output signal 148 of the phase inverter 144. When the set output signal 146 is equal to "true," the flip-flop is set. When the reset output signal 148 is equal to "true," the flip-flop latch 145 is reset. As a result, the oscillation is converted to a square wave with frequency equal to the oscillation frequency of the input signal 102 that exceeds the magnitude threshold 104. It should be appreciated that the phase inverter 144 and the flip-flop latch 145 may be implemented in other configurations without departing from the scope of the present disclosure.

The increase detector 124 receives the square wave signal 136 and generates a tic pulse signal 138. In the example provided, the increase detector 124 generates a tic pulse at each leading edge of the square wave signal 136 oscillation. The period of the tic pulse signal 138 indicates the period of the monitored oscillation. It should be appreciated that other configurations or components may be utilized without departing from the scope of the present disclosure.

Figure 1E:
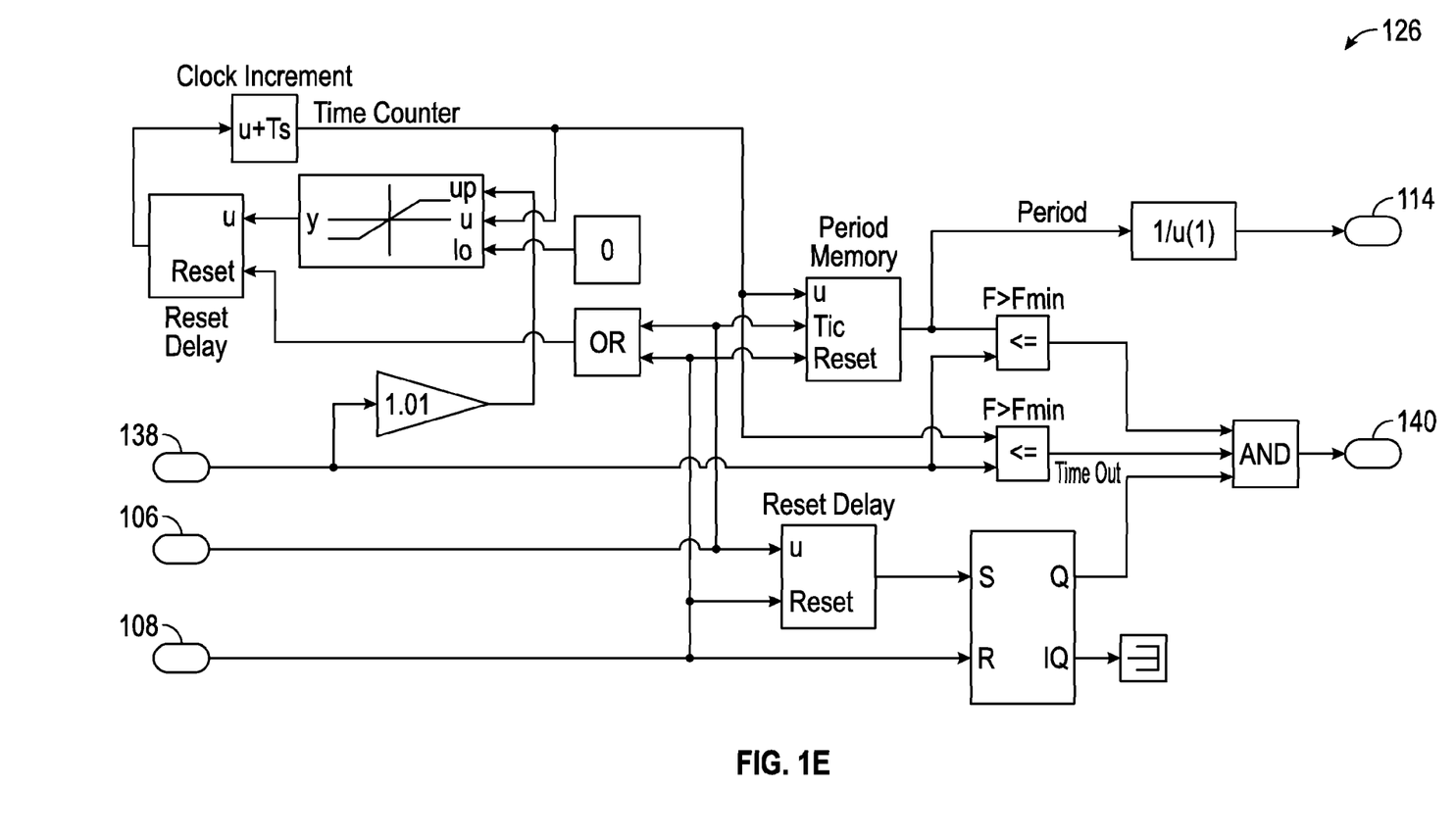

The frequency analyzer 126 receives the tic pulse signal 138, the period threshold 106, and the reset input 108. An example of a frequency analyzer 126 is illustrated in FIG. 1E in accordance with some embodiments. It should be appreciated that other implementations may be incorporated to achieve the features of the frequency analyzer 126 without departing from the scope of the present disclosure. The frequency analyzer 126 calculates the frequency of oscillation from the tic pulse signal 138 and generates the frequency signal 114 by applying inversion to the period of tic pulse signal 138. In some embodiments, protection against division by zero is provided, as will be appreciated by those with skill in the art. The frequency analyzer 126 further generates an "in-range" signal 140 when the measured frequency is in the range of interest as indicated by the period threshold 106.

Figure 1F:
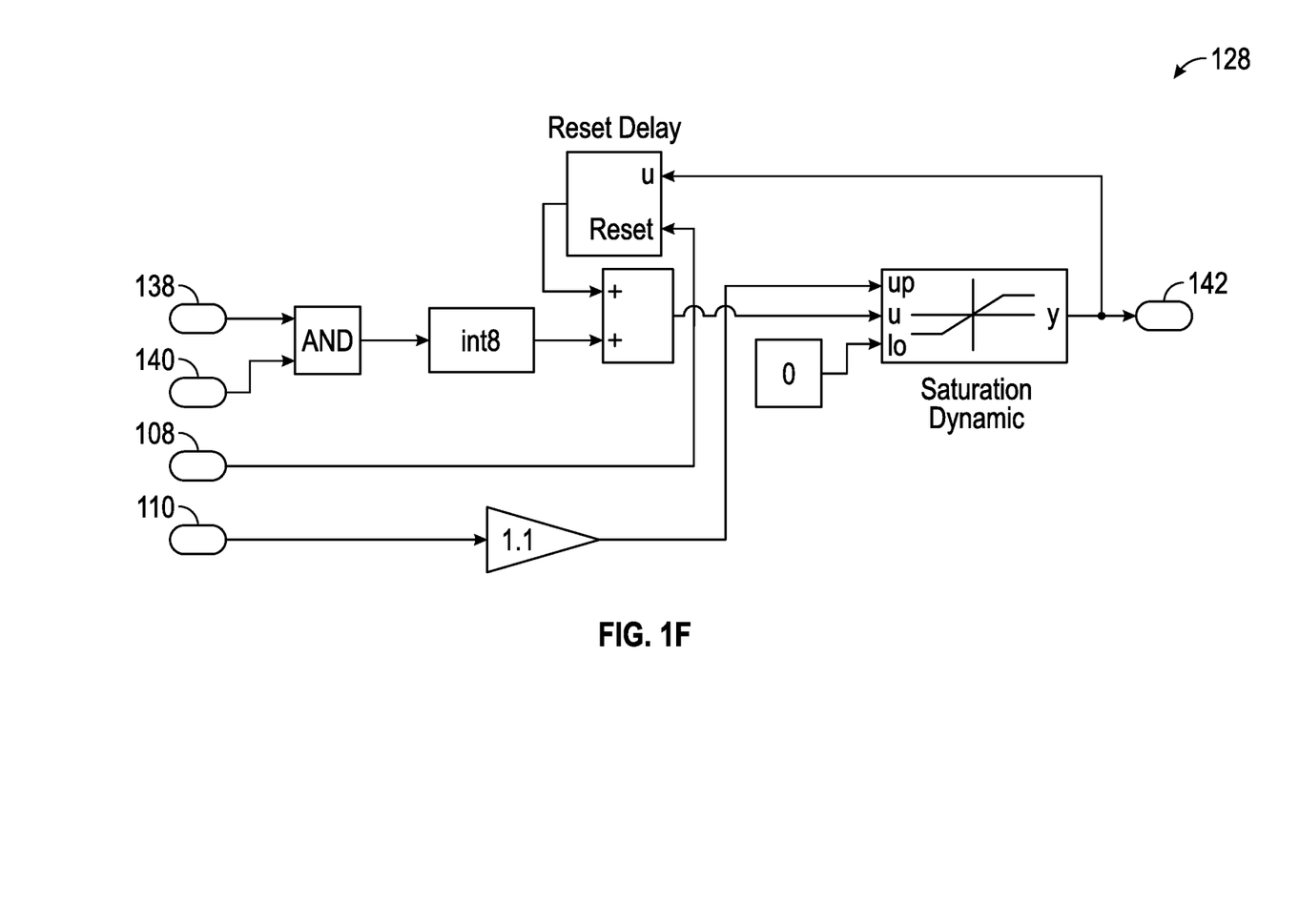

The counter 128 receives the tic pulse signal 138, the in-range signal 140, the persistency threshold 110, and the reset input 108. The counter 128 counts the number of cycles of the oscillations with magnitude that exceed the magnitude threshold 104 and have frequency higher than the frequency threshold as indicated by the period threshold 106. In the example provided, the counter 128 counts one cycle for every tic pulse received after the first tic pulse. The counter 128 generates a counted cycles signal 142 that indicates the number of cycles counted. In the example provided, the counted cycles do not decrement when the oscillations disappear. An example of the counter is illustrated in FIG. 1F in accordance with some embodiments. It should be appreciated that other implementations may be incorporated to achieve the features of the counter 128 without departing from the scope of the present disclosure.

The persistency comparison block 130 receives the counted cycles signal 142 and generates the failure signal 116 when the counted cycles exceed a number of cycles indicated by the persistency threshold 110. The comparison block 130 compares the counted number of cycles against the persistency threshold 110, which is defined in number of cycles in the example provided. When the number of cycles is equal to or higher than the persistency threshold 110, the module 100 flags an oscillatory failure. In the example provided, the fault is latched outside the module 100 for the rest of the flight.

Figure 2A:
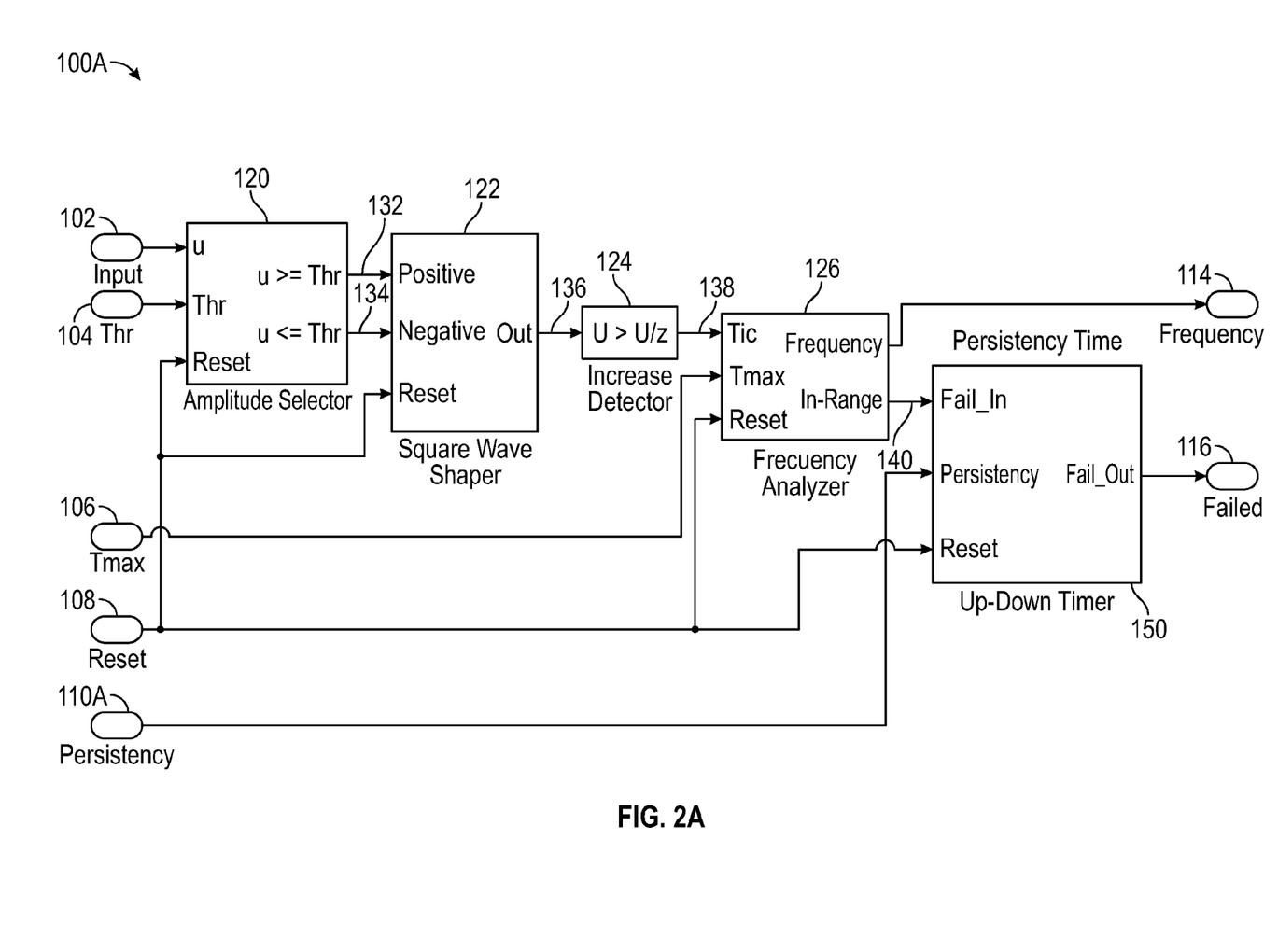
FIG. 2A is a simplified block diagrams of an oscillation monitoring module according to some embodiments.
Figure 2B:
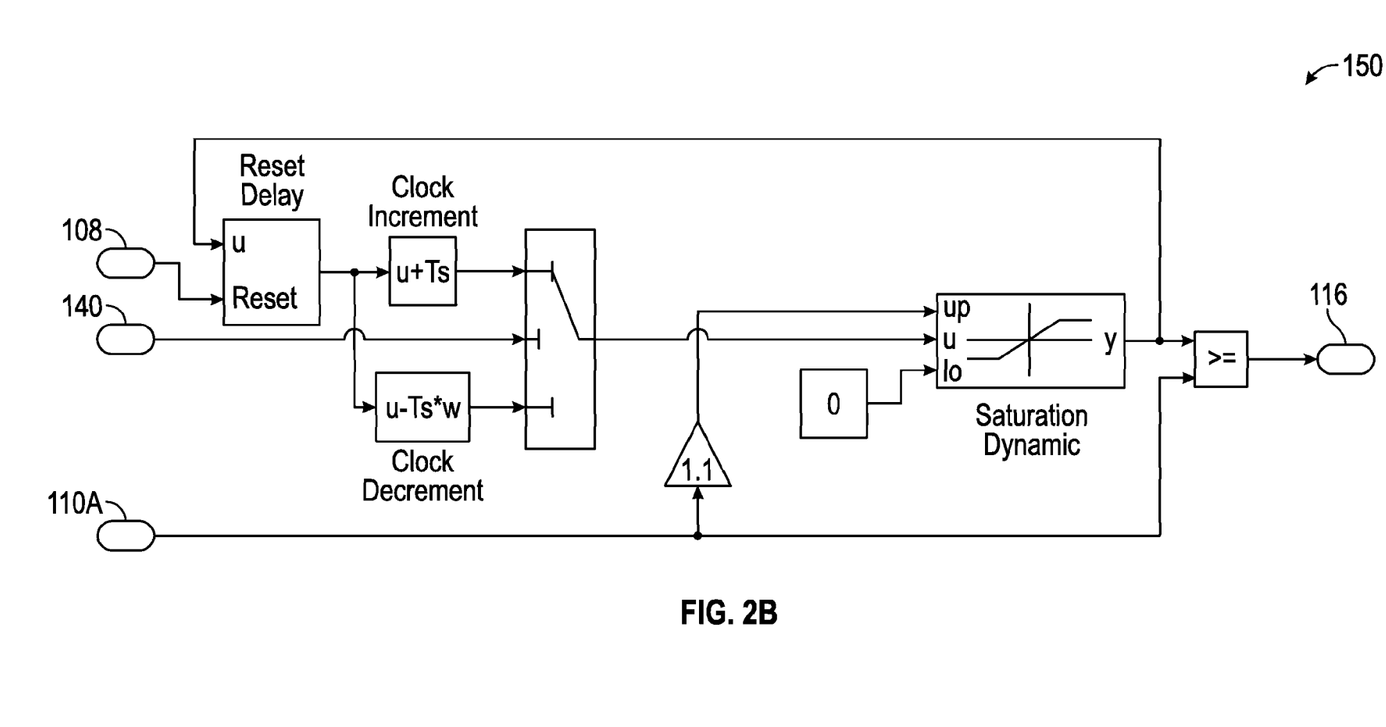

Referring now to FIG. 2A, an oscillation monitoring module 100A is illustrated in accordance with some embodiments. The oscillation monitoring module 100A is similar to the oscillation monitoring module 100, where like number refer to like components. The module 100A, however, receives a persistency threshold 110A and includes a timer 150. The persistency threshold 110A indicates a threshold time for the in-range signal 140 to be received at the timer 150. The timer 150 receives the in-range signal 140 and the persistency threshold 110A. When the timer 150 has received the in-range signal 140 for more time than is indicated by the persistency threshold 110A, then the timer 150 generates the failure signal 116. In the example provided, the timer 150 is an up-down timer that decrements the counted time at a rate equal to 20% of the incremental rate when the in-range signal 140 is not received in order to detect intermittent oscillatory failures. An example of the timer 150 is illustrated in FIG. 2B in accordance with some embodiments. It should be appreciated that other implementations may be incorporated to achieve the features of the timer 150 without departing from the scope of the present disclosure.

Figure 3:
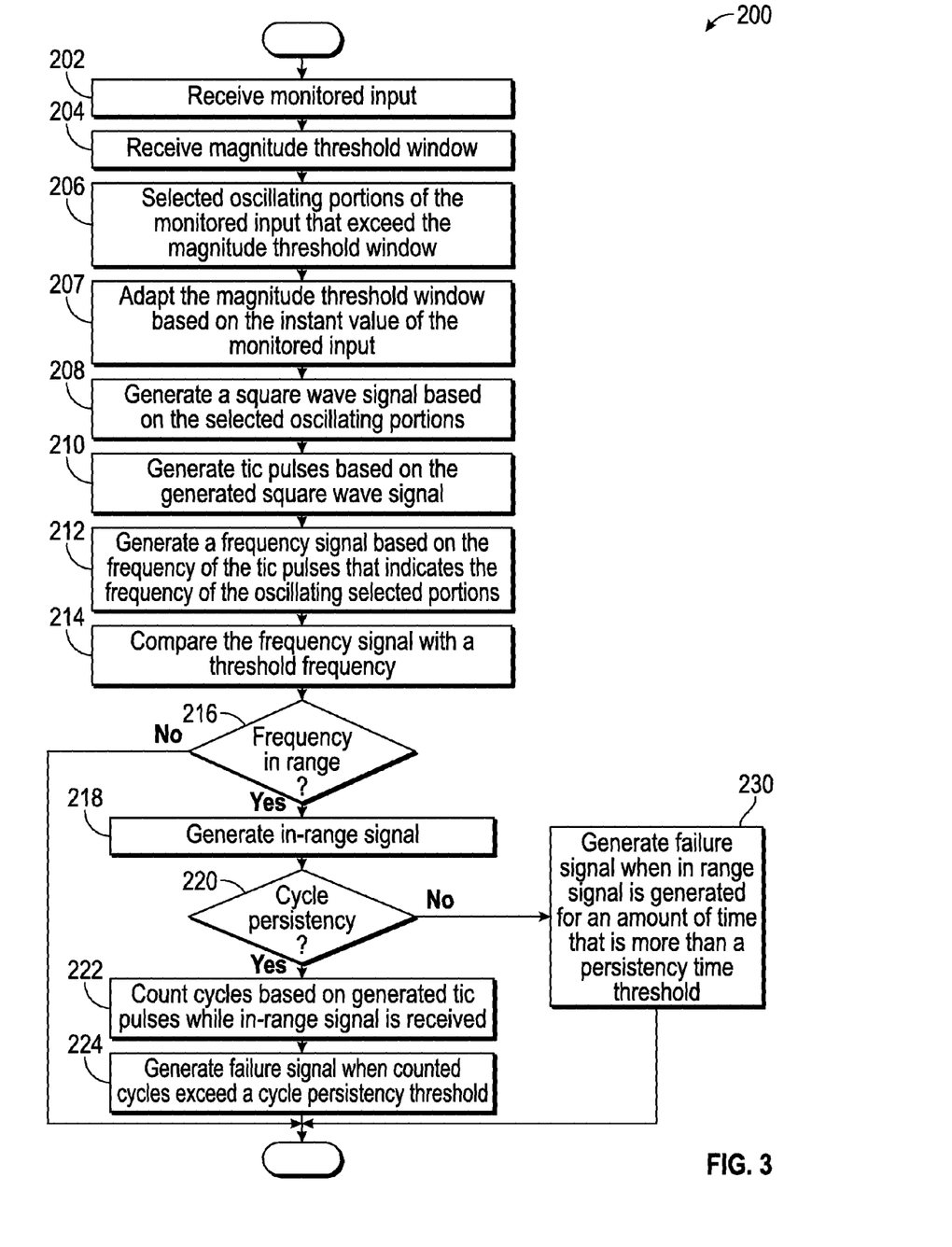
FIG. 3 is a flow diagram illustrating a method of monitoring oscillations according to some embodiments.

Referring now to FIG. 3, operations 200 for monitoring oscillations are illustrated in accordance with some embodiments. In the example provided, the operations 200 are performed by the module 100 or the module 100A. It should be appreciated that the operations 200 may be performed by other modules implemented in software, hardware, or a combination of software and hardware.

A monitored input is received in operation 202 and a magnitude threshold window is received in operation 204. For example, the module 100 may receive the input signal 102 and the magnitude threshold 104 to define the upper and lower thresholds of the window.

Oscillating portions of the monitored input that exceed the magnitude threshold window are selected in operation 206. The oscillating portions are defined in time, so that a portion is a time segment of the signal during which the magnitude of the input exceeds the magnitude threshold window. For example, the amplitude selector 120 of the module 100 may select the portions by generating the signals 132, 134 during the times when the input signal 102 exceeds the upper threshold 137 or the lower threshold 139.

The magnitude threshold window is adapted in operation 207 based on the instant value of the monitored input. For example, as described above, the amplitude selector 120 may increase or decrease the upper and lower thresholds 137, 139 based on an instant value of the input signal 102 when the input signal 102 exceeds the upper threshold 137 or the lower threshold 139.

A square wave signal is generated in operation 208 based on the selected oscillating portions. For example, the square wave shaper 122 may generate the square wave signal 136 based on the signals 132, 134. Tic pulses are generated in operation 210 based on the square wave signal. For example, the increase detector 124 of the module 100 may generate the tic pulse signal 138 based on the square wave signal 136.

In operation 212 a frequency signal is generated based on the frequency of the tic pulses. The frequency of the tic pulses indicates the frequency of the selected portions. For example, the frequency analyzer 126 may generate the frequency signal 114 on an output of the module 100.

In operation 214 the frequency signal is compared with a threshold frequency. For example, the frequency analyzer 126 may compare the frequency signal 114 with a frequency threshold based on the period threshold 106. When the frequency signal is in range (exceeds frequency threshold), then decision operation 216 directs the operations to generate an in-range signal in operation 218. For example, the frequency analyzer 126 may generate the in-range signal 140.

At decision operation 220 it is determined whether persistency of the in-range oscillations is to be determined by a number of cycles of the input signal that exceed the thresholds. It should be appreciated that operation 220 may be omitted. For example, the module 100 determines persistency using cycles and the module 100A determines persistency using elapsed time.

When persistency is determined in cycles, the cycles are counted based on the generated tic pulses while the in-range signal is received at operation 222. A failure signal is generated when the counted cycles exceed a cycle persistency threshold at operation 224. For example, the counter 128 of the module 100 may count cycles based on the tic pulse signal 138 and the in-range signal 140 to compare with the persistency threshold 110. The persistency comparison block 130 may then generate the failure signal 116 when the counted cycles exceed the cycles indicated by the cycle persistency threshold 110.

When persistency is not determined in cycles, operation 230 is performed to generate a failure signal when the in-range signal is generated for an amount of time that is more than a persistency time threshold. For example, the timer 150 of the module 100A may generate the failure signal 116.

Figure 4:
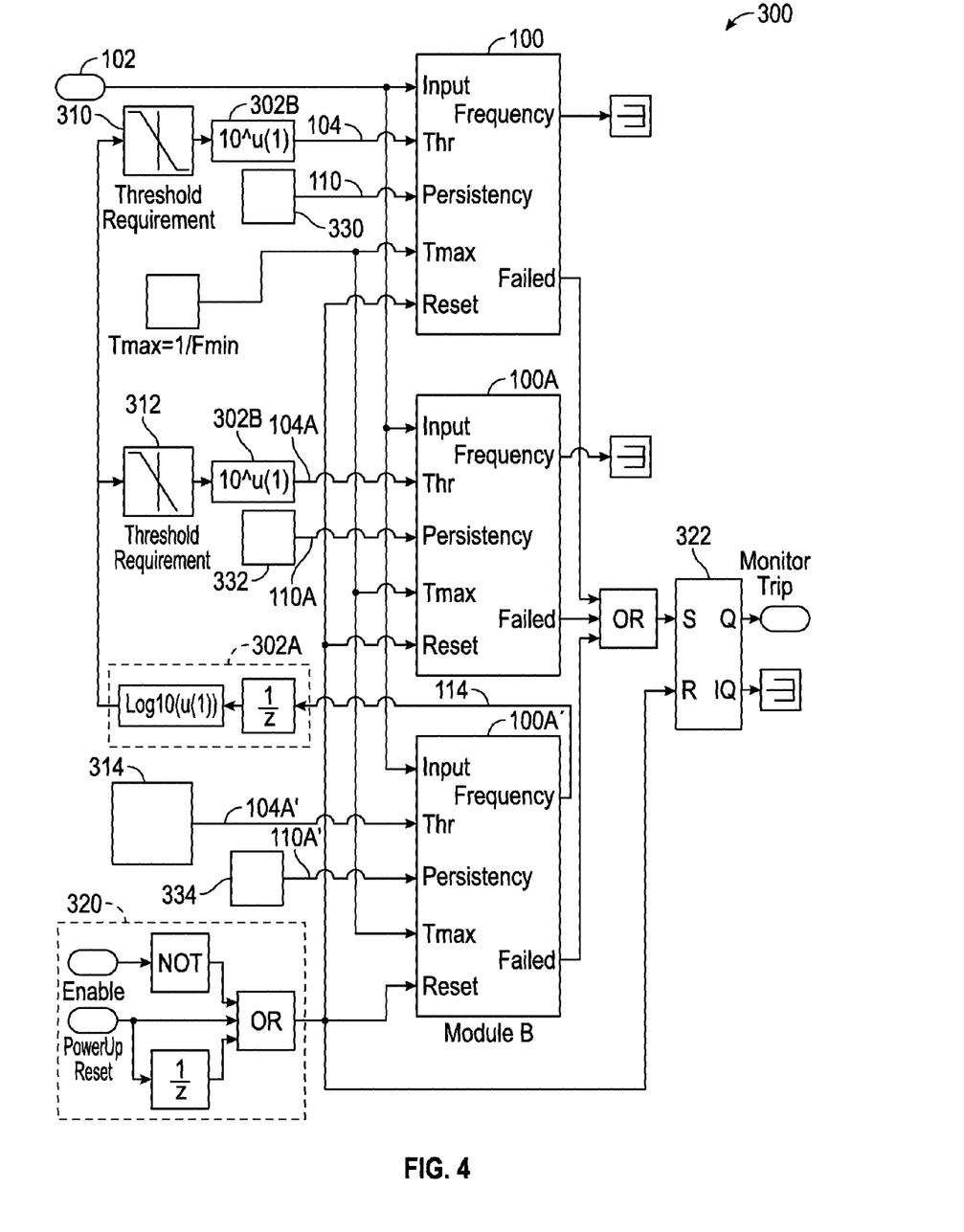
FIG. 4 is a simplified block diagram of an exemplary oscillatory fault monitor according to some embodiments.

Referring now to FIG. 4, an oscillatory fault monitor 300 is illustrated in accordance with some embodiments. In some embodiments, the oscillatory fault monitor 300 is a software program executed by the computer system 101. Although the monitor 300 is described with respect to flight control system monitoring, it should be appreciated that the monitor 300 may be utilized to monitor oscillations in other aircraft systems or other types of applications and environments. In some embodiments, the monitor 300 may be implemented in an application specific integrated circuit (ASIC), an electronic circuit, a processor (shared, dedicated, or group) and memory that execute one or more software or firmware programs, a combinational logic circuit, and/or other suitable components that provide the described functionality.

The monitor 300 includes a first oscillation monitoring module 100, a second oscillation monitoring module 100A, a third oscillation monitoring module 100A', a first conversion block 302A, second conversion blocks 302B, a first magnitude requirement 310, a second magnitude requirement 312, a third magnitude requirement 314, a reset block 320, and an output latch 322. The third oscillation monitoring module 100A' is substantially similar to the second oscillation monitoring module 100A, but is renumbered for clarity of differentiation between the second oscillation monitoring module 100A and the third oscillation monitoring module 100A' as implemented in the monitor 300. It should be appreciated that any number of modules 100 or 100A greater than one may be incorporated without departing from the scope of the present disclosure.

The input signal 102 is supplied to each of the modules 100, 100A, 100A'. For example, the input signal 102 may be supplied by a fly-by-wire flight control system in an aircraft or may represent an error signal indicating a difference between a command and a response. The first conversion block 302A converts the linear output signal 114 to a logarithmic scale for use with the logarithmic magnitude requirements 310, 312 and includes a delay block to resolve the algebraic loop. The second conversion blocks 302B convert the logarithmic output of the magnitude requirements 310, 312 to linear scale for use by the modules 100, 100A. It should be appreciated that the conversion blocks 302 may be omitted where no conversion is desired. The magnitude threshold 104 for module 100, threshold 104A for module 100A, and threshold 104A' for module 100A' are generated based on the respective magnitude requirement 310, 312, 314.

The monitor 300 further stores persistency requirements 330, 332, 334 for each of the modules 100, 100A, 100A'. The persistency requirements indicate a maximum amount of time or cycles that oscillations of the input signal 102 may exceed a magnitude and frequency threshold. For example, the first oscillation monitoring module 100 has a first persistency requirement 330 that is measured in cycles, while the second oscillation monitoring module 100A has a second persistency requirement 332 measured in an amount of time, and the third oscillation monitoring module 100A' has a third persistency requirement 334 measured in an amount of time. In the example provided, the first persistency requirement 330 is more strict than the second persistency requirement 332, and the second persistency requirement 332 is more strict than the third persistency requirement 334, as will be appreciated by those with skill in the art. Persistency thresholds 110, 110A, 110A' are generated based on the respective persistency requirements 330, 332, 334.

Figure 5:
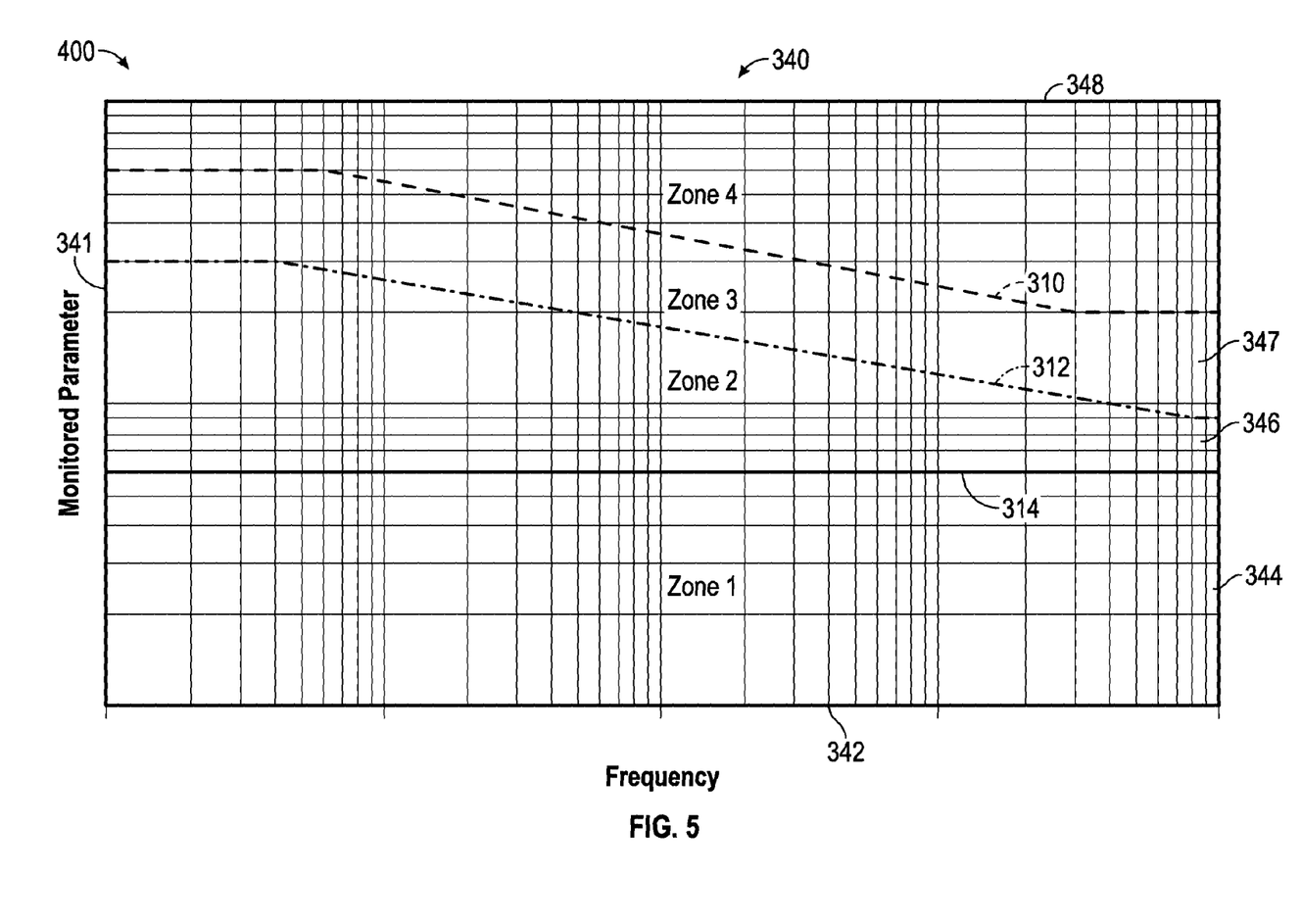
FIG. 5 is a graphical representation of exemplary oscillatory fault detection requirements according to some embodiments.

In general, the size of the magnitude threshold window is driven by the frequency signal generated in the frequency analyzer located in the module with the lowest amplitude threshold. An example of oscillatory fault detection requirements 340 is illustrated in FIG. 5. The magnitude of the oscillation is depicted on the vertical axis 341 and the frequency of the oscillation is depicted on the horizontal axis 342. The first magnitude requirement 310 and the second magnitude requirement 312 depend on the frequency of the oscillations of the input signal 102. In the example provided, the third magnitude requirement 314 is a constant value and the magnitude requirements 310, 312 are implemented as lookup tables that generate the magnitude thresholds 104 and 104A based on the frequency signal 114 output of the third oscillation monitoring module 100A'.

The third magnitude requirement 314 and the horizontal axis 342 define a first zone 344 in which oscillations at any frequency may be received without tripping the fault detector. The second and third magnitude requirements 312, 314 define a second zone 346 in which the third oscillation monitoring module 100A' will trip the fault monitor when the oscillations last longer than the third persistency requirement 334. The first and second requirements 310, 312 define a third zone 347 in which the second oscillation monitoring module 100A will trip the fault monitor when the oscillations last longer than the second persistency requirement 332. Oscillations with magnitude greater than the first magnitude requirement 310 define a fourth zone 348 in which the first module 100 will trip the fault monitor when the oscillations last longer than the first persistency requirement 330. It should be appreciated that the requirements may vary considerably from those presented without departing from the scope of the present disclosure. Accordingly, the threshold window is adaptive to both the frequency of oscillations to adjust the threshold window size and to the value of the signal received by movement of the upper and lower thresholds.

Figure 6:
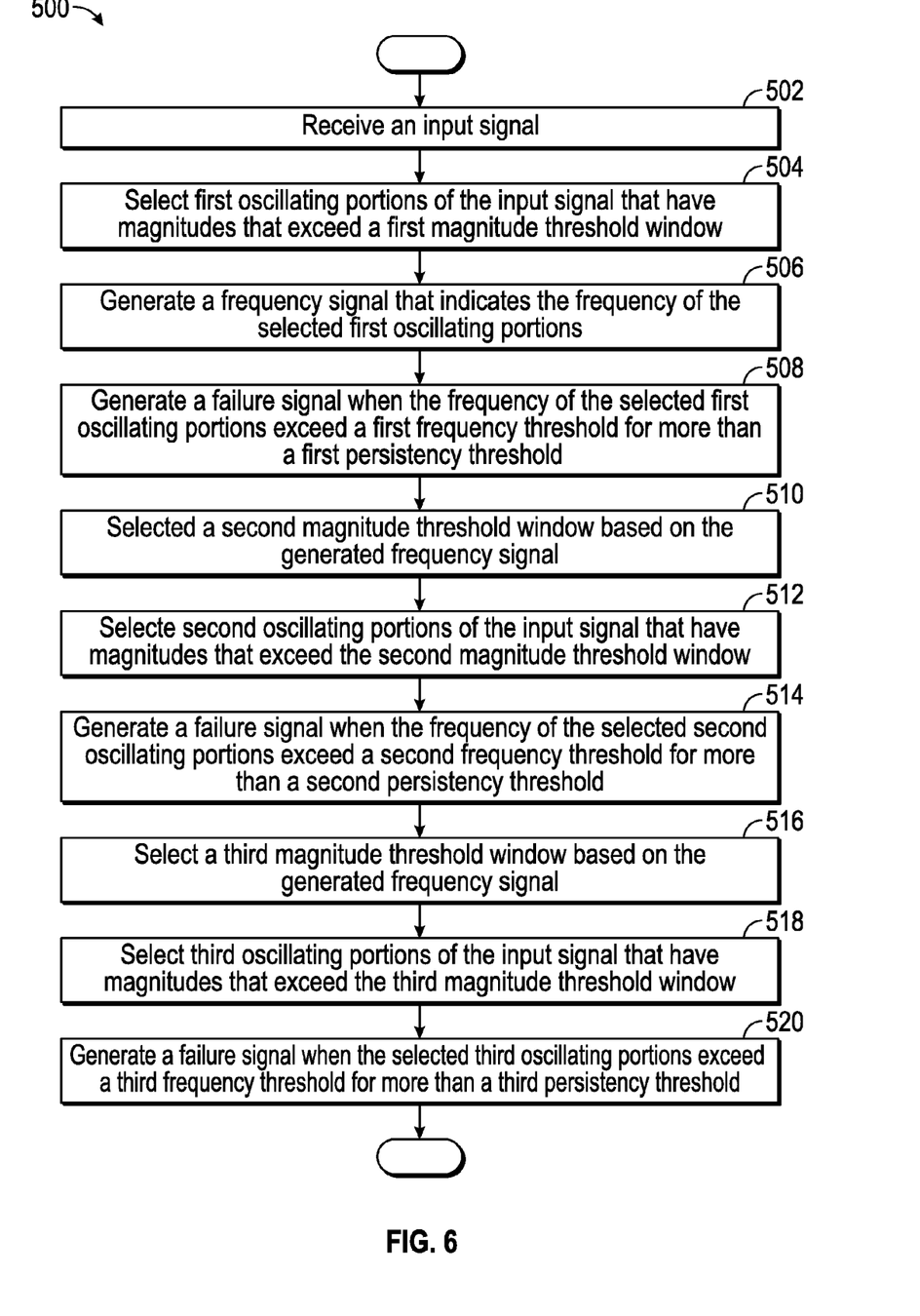
FIG. 6 is a flow diagram illustrating a method of monitoring oscillations according to some embodiments.

Referring now to FIG. 6, a flow diagram illustrates operations 500 for monitoring oscillations according to some embodiments. An input signal is received at operation 502. For example, the input signal 102 may be received by the first, second, and third oscillation monitoring modules 100, 100A, 100A'.

First oscillating portions of the input signal are selected at operation 504. The first oscillating portions are selected as time segments of the input signal that exceed a first magnitude threshold window. A frequency signal is generated in operation 506 to indicate the oscillation frequency of the first oscillating portions. A failure signal is generated at operation 508 when the frequency of the selected first oscillating portions exceed a first frequency threshold for more than a first persistency threshold. For example, the third oscillation monitoring module 100A' may select oscillating portions of the input signal 102 with magnitude greater than the third magnitude requirement 314 (located in the second, third, or fourth zones 346, 347, 348) for longer than the third persistency requirement 334.

A second magnitude threshold window is selected at operation 510 based on the generated frequency signal. For example, the magnitude threshold 104 sent to the second oscillation monitoring module 100A may be selected based on the value of the second magnitude requirement 312 at the location on the horizontal axis 342 of the requirements 340 indicated by the frequency signal 114 generated by the third oscillation monitoring module 100A'. Second oscillating portions of the input signal are selected at operation 512. The second oscillating portions are selected as time segments of the input signal that exceed a second magnitude threshold window. A failure signal is generated at operation 514 when the frequency of the selected second oscillating portions exceeds a second frequency threshold for more than a second persistency threshold. For example, the second oscillation monitoring module 100A may select oscillating portions of the input signal 102 with magnitude greater than the second magnitude requirement 312 (located in the third or fourth zones 347, 348) for longer than the second persistency requirement 332.

A third magnitude threshold window is selected at operation 516 based on the generated frequency signal. For example, the magnitude threshold 104 sent to the first module 100 may be selected based on the value of the first magnitude requirement 310 at the location on the horizontal axis 342 of the requirements 340 indicated by the frequency signal 114 generated by the third oscillation monitoring module 100A'. Third oscillating portions of the input signal are selected at operation 518. The third oscillating portions are selected as time segments of the input signal that exceed a third magnitude threshold window. A failure signal is generated at operation 520 when the frequency of the selected third oscillating portions exceed a third frequency threshold for more than a third persistency threshold. For example, the first oscillation monitoring module 100 may select oscillating portions of the input signal 102 with magnitude greater than the first magnitude requirement 310 (located in the fourth zone 348) for longer than the first persistency requirement 330.

A data structure representative of the computer system 101 and/or portions thereof included on a computer readable storage medium may be a database or other data structure which can be read by a program and used, directly or indirectly, to fabricate the hardware comprising the computer system 101. The operations illustrated in FIG. 3 and FIG. 6 may be governed by instructions that are stored in a non-transitory computer readable storage medium and that are executed by at least one processor of a computing system. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

The modules and operations provide numerous advantages over prior systems and methods. For example, the principles of the disclosure permit a simple, fully analyzable, and testable implementation design that is robust to nuisance trips. Furthermore, monitors have flexibility to be tuned directly to frequency based requirements curves via simple lookup tables. Parallel monitoring structures for multiple frequency sub-ranges are not required and complex amplitude detection curves may be incorporated with use of the oscillation detection modules. Additionally, the sampling rate of the monitor may be adjusted to balance signal fidelity and resolution with computational burden. Furthermore, because monitor performance does not depend on input signal waveform, the monitor may be tuned precisely to the requirements curves. The monitor is capable of detecting oscillations in a random waveform, varying amplitude & random frequency waveform; multi-harmonic oscillations, pseudo-noise oscillations, and "solid" & "liquid" oscillatory faults, among others.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An aircraft system comprising:
a third oscillation monitoring module configured to:
   select third oscillating portions of an input signal;
   generate a frequency signal that indicates a frequency of the third oscillating portions; and
   generate a third failure signal in response to the frequency of the third oscillating portions exceeding third oscillatory fault detection requirements for the input signal; and
a second oscillation monitoring module configured to:
   select second oscillating portions of the input signal based on the frequency signal generated by the third oscillation monitoring module; and
   generate a second failure signal in response to a frequency of the second oscillating portions exceeding second oscillatory fault detection requirements for the input signal.

2. The aircraft system of claim 1, wherein the second oscillation monitoring module is further configured to select the second oscillating portions based on a second magnitude threshold window that is based on the frequency signal generated by the third oscillation monitoring module.

3. The aircraft system of claim 1, wherein the third oscillation monitoring module is further configured to generate the third failure signal in response to the frequency of the third oscillating portions exceeding a third frequency threshold for more time or more cycles than indicated by a third persistency threshold.

4. The aircraft system of claim 1, wherein the second oscillation monitoring module is further configured to generate the second failure signal in response to the frequency of the second oscillating portions exceeding a second frequency threshold for more time or more cycles than indicated by a second persistency threshold.

5. The aircraft system of claim 1, wherein the third oscillation monitoring module is further configured to select time segments of the input signal during which a magnitude of the input signal equals or exceeds an upper threshold or a lower threshold of a third magnitude threshold window to select the third oscillating portions.

6. The aircraft system of claim 5, wherein the third oscillation monitoring module is further configured to adapt the third magnitude threshold window based on an instant value of the input signal in response to the input signal exceeding the upper threshold or lower threshold of the third magnitude threshold window.

7. The aircraft system of claim 1, wherein the second oscillation monitoring module is further configured to select time segments of the input signal during which a magnitude of the input signal equals or exceeds an upper threshold or a lower threshold of a second magnitude threshold window to select the second oscillating portions.

8. The aircraft system of claim 7, wherein the second oscillation monitoring module is further configured to adapt the second magnitude threshold window based on an instant value of the input signal in response to the input signal exceeding the upper threshold or lower threshold of the second magnitude threshold window.

9. The aircraft system of claim 1, further comprising a first oscillation monitoring module configured to:
   select first oscillating portions of the input signal based on the frequency signal generated by the third oscillation monitoring module; and
   generate a first failure signal in response to a frequency of the first oscillating portions exceeding first oscillatory fault detection requirements for the input signal.

10. The aircraft system of claim 9, wherein the first oscillation monitoring module is further configured to select the first oscillating portions based on a first magnitude threshold window that is based on the frequency signal generated by the third oscillation monitoring module.

11. The aircraft system of claim 9, wherein the first oscillation monitoring module is further configured to generate the first failure signal in response to the frequency of the first oscillating portions exceeding a first frequency threshold for more time or more cycles than indicated by a first persistency threshold.

12. The aircraft system of claim 9, wherein the first oscillation monitoring module is further configured to select time segments of the input signal during which a magnitude of the input signal equals or exceeds an upper threshold or a lower threshold of a first magnitude threshold window to select the first oscillating portions.

13. The aircraft system of claim 12, wherein the first oscillation monitoring module is further configured to adapt the first magnitude threshold window based on an instant value of the input signal in response to the input signal exceeding the upper threshold or lower threshold of the first magnitude threshold window.

14. A non-transitory computer readable medium storing instructions for execution by a processor, the instructions configured to cause a processor to:
   select third oscillating portions of an input signal with a third oscillation monitoring module;
   generate a frequency signal that indicates a frequency of the third oscillating portions;
   generate a third failure signal in response to the frequency of the third oscillating portions exceeding third oscillatory fault detection requirements for the input signal;
   select second oscillating portions of the input signal based on the frequency signal generated by the third oscillation monitoring module; and
   generate a second failure signal at a second oscillation monitoring module in response to a frequency of the second oscillating portions exceeding second oscillatory fault detection requirements for the input signal.

15. The non-transitory computer readable medium of claim 14, wherein the instructions are further configured to cause a processor to:
   select first oscillating portions of the input signal based on the frequency signal generated by the third oscillation monitoring module; and
   generate a first failure signal at a first oscillation monitoring module in response to a frequency of the first oscillating portions exceeding first oscillatory fault detection requirements for the input signal.

16. The non-transitory computer readable medium of claim 15, wherein the instructions are further configured to cause a processor to:
   select the second oscillating portions based on a second magnitude threshold window that is based on the frequency signal generated by the third oscillation monitoring module; and select the first oscillating portions based on a first magnitude threshold window that is based on the frequency signal generated by the third oscillation monitoring module.

17. The non-transitory computer readable medium of claim 14, wherein the instructions are further configured to cause a processor to:
select time segments of the input signal during which a magnitude of the input signal equals or exceeds an upper threshold or a lower threshold of a third magnitude threshold window to select the third oscillating portions;
adapt the third magnitude threshold window based on an instant value of the input signal in response to the input signal exceeding the upper threshold or lower threshold of the third magnitude threshold window;
select time segments of the input signal during which a magnitude of the input signal equals or exceeds an upper threshold or a lower threshold of a second magnitude threshold window to select the second oscillating portions; and
adapt the second magnitude threshold window based on an instant value of the input signal in response to the input signal exceeding the upper threshold or lower threshold of the second magnitude threshold window.

18. A method of monitoring oscillations of an input signal, the method comprising:
selecting third oscillating portions of the input signal with a third oscillation monitoring module;
generating a frequency signal that indicates a frequency of the third oscillating portions;
generating a third failure signal in response to the frequency of the third oscillating portions exceeding third oscillatory fault detection requirements for the input signal;
selecting second oscillating portions of the input signal based on the frequency signal generated by the third oscillation monitoring module; and
generating a second failure signal at a second oscillation monitoring module in response to a frequency of the second oscillating portions exceeding second oscillatory fault detection requirements for the input signal.

19. The method of claim 18, further comprising:
selecting first oscillating portions of the input signal based on the frequency signal generated by the third oscillation monitoring module; and
generating a first failure signal at a first oscillation monitoring module in response to a frequency of the first oscillating portions exceeding first oscillatory fault detection requirements for the input signal.

20. The method of claim 19, further comprising:
selecting the second oscillating portions based on a second magnitude threshold window that is based on the frequency signal generated by the third oscillation monitoring module; and
selecting the first oscillating portions based on a first magnitude threshold window that is based on the frequency signal generated by the third oscillation monitoring module.

* * * * *